(12) United States Patent
Ross

(10) Patent No.: US 7,306,605 B2
(45) Date of Patent: Dec. 11, 2007

(54) ANTERIOR CERVICAL PLATE

(75) Inventor: Thomas Ross, Austin, TX (US)

(73) Assignee: Zimmer Spine, Inc., Minneapolis, MN (US)

( * ) Notice: Subject to any disclaimer, the term of this patent is extended or adjusted under 35 U.S.C. 154(b) by 440 days.

(21) Appl. No.: 10/676,064

(22) Filed: Oct. 2, 2003

(65) Prior Publication Data

US 2005/0075633 A1 Apr. 7, 2005

(51) Int. Cl.
A61B 17/58 (2006.01)
(52) U.S. Cl. .............. 606/61; 606/69; 606/71
(58) Field of Classification Search ......... 606/61, 606/69, 70, 71
See application file for complete search history.

(56) References Cited

U.S. PATENT DOCUMENTS

| 4,288,902 | A | 9/1981 | Franz |
| 5,180,381 | A | 1/1993 | Aust et al. |
| 5,344,421 | A | 9/1994 | Crook |
| 5,364,399 | A | 11/1994 | Lowery et al. |
| 5,439,472 | A * | 8/1995 | Evans et al. ......... 606/176 |
| 5,549,612 | A | 8/1996 | Yapp et al. |
| 5,931,838 | A | 8/1999 | Vito |
| 5,951,558 | A * | 9/1999 | Fiz .................. 606/70 |
| 5,954,722 | A | 9/1999 | Bono |
| 6,152,927 | A | 11/2000 | Farris et al. |
| 6,193,721 | B1 * | 2/2001 | Michelson ............ 606/70 |
| D440,311 | S | 4/2001 | Michelson |
| 6,224,602 | B1 * | 5/2001 | Hayes .............. 606/69 |
| 6,235,034 | B1 | 5/2001 | Bray |
| 6,258,089 | B1 | 7/2001 | Campbell et al. |
| D449,692 | S | 10/2001 | Michelson |
| 6,306,139 | B1 | 10/2001 | Fuentes |
| 6,331,179 | B1 | 12/2001 | Freid et al. |
| 6,383,186 | B1 | 5/2002 | Michelson |
| 6,398,783 | B1 | 6/2002 | Michelson |
| 6,402,756 | B1 | 6/2002 | Ralph et al. |
| 6,413,259 | B1 | 7/2002 | Lyons et al. |
| 6,416,528 | B1 | 7/2002 | Michelson |
| 6,428,542 | B1 | 8/2002 | Michelson |
| 6,454,733 | B1 | 9/2002 | Krusenklaus |
| 6,454,769 | B2 | 9/2002 | Wagner et al. |
| 6,454,771 | B1 | 9/2002 | Michelson |
| 6,458,133 | B1 | 10/2002 | Lin |
| 6,503,250 | B2 | 1/2003 | Paul |

(Continued)

OTHER PUBLICATIONS

Encore Medical Corporation Brochure, SECUPLATE® Anterior Cervical Plate, 2001.

(Continued)

Primary Examiner—Eduardo C. Robert
Assistant Examiner—James L. Swiger
(74) Attorney, Agent, or Firm—Wood, Herron & Evans, LLP

(57) ABSTRACT

An anterior cervical plate has a lower surface adapted to engage the cervical spine and a top surface. At least one location along the plate there are two transversely aligned bone screw holes. A locking element is pivotally mounted between these two bone screw holes for movement between an open position which uncovers the two bone screw holes and a locking position wherein the locking element at least partially covers each of the two bone screw holes. A positive positioning structure positively positions the locking element in the locking position.

16 Claims, 10 Drawing Sheets

U.S. PATENT DOCUMENTS

| | | |
|---|---|---|
| 6,527,776 B1 | 3/2003 | Michelson |
| 6,533,786 B1 | 3/2003 | Needham et al. |
| 6,571,671 B1* | 6/2003 | Giannetti .................. 82/160 |
| 6,572,619 B2 | 6/2003 | Santilli |
| 6,585,738 B1 | 7/2003 | Mangione et al. |
| 6,592,586 B1 | 7/2003 | Michelson |
| 6,595,993 B2 | 7/2003 | Donno et al. |
| 6,599,290 B2 | 7/2003 | Bailey et al. |
| 6,602,255 B1 | 8/2003 | Campbell et al. |
| 6,602,256 B1 | 8/2003 | Hayes |
| 6,602,257 B1 | 8/2003 | Thramann |
| 6,616,666 B1 | 9/2003 | Michelson |
| 6,620,163 B1 | 9/2003 | Michelson |
| 6,626,907 B2 | 9/2003 | Campbell et al. |
| 6,652,525 B1 | 11/2003 | Assaker et al. |
| 6,666,867 B2 | 12/2003 | Ralph et al. |
| 6,679,883 B2 | 1/2004 | Hawkes et al. |
| 6,689,134 B2 | 2/2004 | Ralph et al. |
| 6,692,503 B2 | 2/2004 | Foley et al. |
| 6,695,846 B2 | 2/2004 | Richelsoph et al. |
| 6,699,249 B2 | 3/2004 | Schlapfer et al. |
| 6,706,005 B2 | 3/2004 | Roy et al. |
| 6,712,818 B1 | 3/2004 | Michelson |
| 6,755,833 B1 | 6/2004 | Paul et al. |
| 6,855,147 B2 | 2/2005 | Harrington, Jr. |
| 6,890,335 B2 | 5/2005 | Grabowski et al. |
| 6,916,320 B2 | 7/2005 | Michelson |
| 6,926,718 B1 | 8/2005 | Michelson |
| 6,932,820 B2 | 8/2005 | Osman |
| 6,936,050 B2 | 8/2005 | Michelson |
| 6,936,051 B2 | 8/2005 | Michelson |
| 6,945,973 B2 | 9/2005 | Bray |
| 6,964,664 B2 | 11/2005 | Freid et al. |
| 6,969,390 B2 | 11/2005 | Michelson |
| 6,985,186 B2 | 1/2006 | Kondo et al. |
| 6,989,012 B2 | 1/2006 | LeHuec et al. |
| 7,001,387 B2 | 2/2006 | Farris et al. |
| 7,001,389 B1 | 2/2006 | Navarro et al. |
| 7,004,944 B2 | 2/2006 | Gause |
| 7,008,426 B2 | 3/2006 | Paul |
| 7,025,769 B1 | 4/2006 | Ferree |
| 7,041,105 B2 | 5/2006 | Michelson |
| 7,044,952 B2 | 5/2006 | Michelson |
| 7,048,739 B2 | 5/2006 | Konieczynski et al. |
| 7,060,067 B2 | 6/2006 | Needham et al. |
| 7,070,599 B2 | 7/2006 | Paul |
| 7,074,221 B2 | 7/2006 | Michelson |
| 7,077,843 B2 | 7/2006 | Thramann et al. |
| 7,077,844 B2 | 7/2006 | Michelson |
| 7,097,645 B2 | 8/2006 | Michelson |
| 7,112,202 B2 | 9/2006 | Michelson |
| 7,115,130 B2 | 10/2006 | Michelson |
| 7,118,573 B2 | 10/2006 | Michelson |
| 7,137,984 B2 | 11/2006 | Michelson |
| 7,166,111 B2 | 1/2007 | Kolb et al. |
| 7,169,150 B2 | 1/2007 | Shipp et al. |
| 7,175,623 B2 | 2/2007 | Thramann et al. |
| 7,175,624 B2 | 2/2007 | Konieczynski et al. |
| 7,186,254 B2 | 3/2007 | Dinh et al. |
| 7,186,256 B2 | 3/2007 | Michelson |
| 7,201,753 B2 | 4/2007 | Schlapfer et al. |
| 7,204,837 B2 | 4/2007 | Paul |
| 7,220,263 B2 | 5/2007 | Cordaro |
| 2001/0041894 A1* | 11/2001 | Campbell et al. ............ 606/61 |
| 2002/0004683 A1 | 1/2002 | Michelson |
| 2002/0045896 A1 | 4/2002 | Michelson |
| 2002/0055741 A1* | 5/2002 | Schlapfer et al. ............ 606/71 |
| 2002/0058939 A1 | 5/2002 | Wagner et al. |
| 2002/0120273 A1 | 8/2002 | Needham et al. |
| 2002/0173790 A1 | 11/2002 | Chang et al. |
| 2002/0183754 A1 | 12/2002 | Michelson |
| 2002/0188296 A1* | 12/2002 | Michelson .................. 606/71 |
| 2003/0036759 A1 | 2/2003 | Musso |
| 2003/0078583 A1 | 4/2003 | Biedermann et al. |
| 2003/0149434 A1 | 8/2003 | Paul |
| 2003/0187440 A1 | 10/2003 | Richelsoph et al. |
| 2003/0187441 A1 | 10/2003 | Bolger et al. |
| 2003/0187443 A1 | 10/2003 | Lauryssen et al. |
| 2003/0208204 A1 | 11/2003 | Bailey et al. |
| 2003/0225409 A1 | 12/2003 | Fried et al. |
| 2003/0236528 A1 | 12/2003 | Thramann |
| 2004/0019353 A1 | 1/2004 | Fried et al. |
| 2004/0030336 A1 | 2/2004 | Khanna |
| 2004/0030338 A1 | 2/2004 | Paul |
| 2004/0039387 A1 | 2/2004 | Gause et al. |
| 2004/0087951 A1 | 5/2004 | Khalili |
| 2004/0092939 A1 | 5/2004 | Freid et al. |
| 2004/0097950 A1 | 5/2004 | Foley et al. |
| 2004/0106924 A1 | 6/2004 | Ralph et al. |
| 2004/0127896 A1 | 7/2004 | Lombardo et al. |
| 2004/0127897 A1 | 7/2004 | Freid et al. |
| 2004/0127900 A1 | 7/2004 | Konieczynski et al. |
| 2004/0127902 A1 | 7/2004 | Suzuki et al. |
| 2004/0158246 A1 | 8/2004 | Assaker et al. |
| 2004/0167521 A1 | 8/2004 | De Windt |
| 2004/0181229 A1 | 9/2004 | Michelson |
| 2004/0204712 A1 | 10/2004 | Kolb et al. |
| 2004/0204713 A1 | 10/2004 | Addou |
| 2004/0210217 A1 | 10/2004 | Baynham et al. |
| 2004/0220571 A1 | 11/2004 | Assaker et al. |
| 2004/0220572 A1 | 11/2004 | Michelson |
| 2004/0236334 A1 | 11/2004 | Michelson |
| 2004/0236335 A1 | 11/2004 | Michelson |
| 2004/0260306 A1 | 12/2004 | Fallin et al. |
| 2005/0010227 A1 | 1/2005 | Paul |
| 2005/0021032 A1 | 1/2005 | Koo |
| 2005/0027297 A1 | 2/2005 | Michelson |
| 2005/0027298 A1 | 2/2005 | Michelson |
| 2005/0038436 A1 | 2/2005 | Michelson |
| 2005/0043732 A1 | 2/2005 | Dalton |
| 2005/0049593 A1 | 3/2005 | Duong et al. |
| 2005/0049595 A1 | 3/2005 | Suh et al. |
| 2005/0059970 A1 | 3/2005 | Kolb |
| 2005/0059971 A1 | 3/2005 | Michelson |
| 2005/0075633 A1 | 4/2005 | Ross |
| 2005/0085816 A1 | 4/2005 | Michelson |
| 2005/0096657 A1 | 5/2005 | Autericque et al. |
| 2005/0107795 A1 | 5/2005 | Morris et al. |
| 2005/0137596 A1 | 6/2005 | Uwaydah |
| 2005/0137597 A1 | 6/2005 | Butler et al. |
| 2005/0149026 A1 | 7/2005 | Butler er al. |
| 2005/0149027 A1 | 7/2005 | Campbell et al. |
| 2005/0177160 A1 | 8/2005 | Baynham et al. |
| 2005/0177161 A1 | 8/2005 | Baynham et al. |
| 2005/0182403 A1 | 8/2005 | Wang et al. |
| 2005/0182404 A1 | 8/2005 | Lauryssen et al. |
| 2005/0187551 A1 | 8/2005 | Orbay et al. |
| 2005/0187552 A1 | 8/2005 | Michelson |
| 2005/0187553 A1 | 8/2005 | Grabowski et al. |
| 2005/0187554 A1 | 8/2005 | Michelson |
| 2005/0192576 A1 | 9/2005 | Michelson |
| 2005/0192577 A1 | 9/2005 | Mosca et al. |
| 2005/0216009 A1 | 9/2005 | Michelson |
| 2005/0216010 A1 | 9/2005 | Michelson |
| 2005/0216011 A1 | 9/2005 | Paul |
| 2005/0228386 A1 | 10/2005 | Ziolo et al. |
| 2005/0234455 A1 | 10/2005 | Binder et al. |
| 2005/0234456 A1 | 10/2005 | Malandain |
| 2005/0240184 A1 | 10/2005 | Osman |
| 2005/0240185 A1 | 10/2005 | Boomer et al. |
| 2005/0261689 A1 | 11/2005 | Lin |
| 2005/0261690 A1 | 11/2005 | Binder et al. |
| 2005/0273105 A1 | 12/2005 | Konieczynski et al. |
| 2005/0283152 A1 | 12/2005 | Lindermann et al. |

| | | |
|---|---|---|
| 2005/0283155 A1 | 12/2005 | Jacene et al. |
| 2005/0288673 A1 | 12/2005 | Catbagen et al. |
| 2006/0009845 A1 | 1/2006 | Chin |
| 2006/0015103 A1 | 1/2006 | Burke |
| 2006/0036249 A1 | 2/2006 | Baynham et al. |
| 2006/0036250 A1 | 2/2006 | Lange et al. |
| 2006/0064097 A1 | 3/2006 | Bray |
| 2006/0079900 A1 | 4/2006 | Mathieu et al. |
| 2006/0079901 A1 | 4/2006 | Ryan et al. |
| 2006/0085001 A1 | 4/2006 | Michelson |
| 2006/0106387 A1 | 5/2006 | Fanger et al. |
| 2006/0116681 A1 | 6/2006 | Bert |
| 2006/0116683 A1 | 6/2006 | Barrall et al. |
| 2006/0122602 A1 | 6/2006 | Konieczynski et al. |
| 2006/0122603 A1 | 6/2006 | Kolb |
| 2006/0122604 A1 | 6/2006 | Gorhan et al. |
| 2006/0122605 A1 | 6/2006 | Suh et al. |
| 2006/0142766 A1 | 6/2006 | Schafer |
| 2006/0142768 A1 | 6/2006 | Paul |
| 2006/0149251 A1 | 7/2006 | Ziolo et al. |
| 2006/0149252 A1 | 7/2006 | Markworth et al. |
| 2006/0149253 A1 | 7/2006 | Doubler et al. |
| 2006/0149255 A1 | 7/2006 | Doubler et al. |
| 2006/0149256 A1 | 7/2006 | Wagner et al. |
| 2006/0161157 A1 | 7/2006 | Mosca et al. |
| 2006/0167457 A1 | 7/2006 | Suddaby |
| 2006/0173459 A1 | 8/2006 | Kay et al. |
| 2006/0189989 A1 | 8/2006 | Bert |
| 2006/0189990 A1 | 8/2006 | Farris et al. |
| 2006/0195085 A1 | 8/2006 | Happonen et al. |
| 2006/0200134 A1 | 9/2006 | Freid et al. |
| 2006/0200146 A1 | 9/2006 | Doubler et al. |
| 2006/0229620 A1 | 10/2006 | Rothman et al. |
| 2006/0235398 A1 | 10/2006 | Farris et al. |
| 2006/0235403 A1 | 10/2006 | Blain |
| 2006/0235409 A1 | 10/2006 | Blain |
| 2006/0235411 A1 | 10/2006 | Blain et al. |
| 2006/0235412 A1 | 10/2006 | Blain |
| 2006/0235518 A1 | 10/2006 | Blain |
| 2006/0235533 A1 | 10/2006 | Blain |
| 2006/0241611 A1 | 10/2006 | Castro |
| 2006/0241616 A1 | 10/2006 | Konieczynski et al. |
| 2006/0241759 A1 | 10/2006 | Trieu |

OTHER PUBLICATIONS

Surgical Dynamics Brochure, Anterior Cervical Plating System, cover page through p. 10, prior to Sep. of 2002.
Sofamor Danek USA Brochure, ATLANTIS anterior cervical plate system, 1998.
Blackstone Medical Inc. Brochure, Blackstone™ Anterior Cervical Plate, prior to Sep. of 2002.
Alphatec Manufacturing, Inc. Brochure, DELTALOC Anterior Cervical Plate System, prior to Sep. of 2002.
Codman Johnson & Johnson Professional, Inc. Brochure, CODMAN® Anterior Cervical Plate System, prior to Sep. of 2002.
Medtronic Sofamor Danek.—ZEPHIR Anterior Cervical Plate System: Features and Benefits—prior to Sep. of 2002 Access: <http://www.spineuniverse.com/displayarticle.php/article718.html>.
Sofamor Danek USA Brochure, ORION® Anterior Cervical Plate System, 1999.

\* cited by examiner

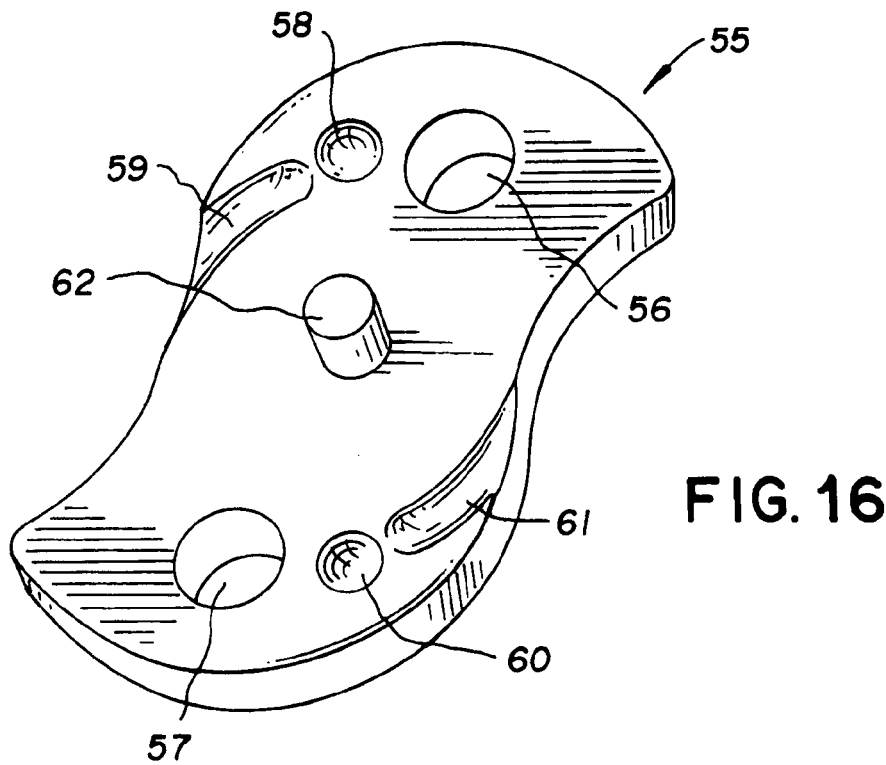
FIG. 16
FIG. 17
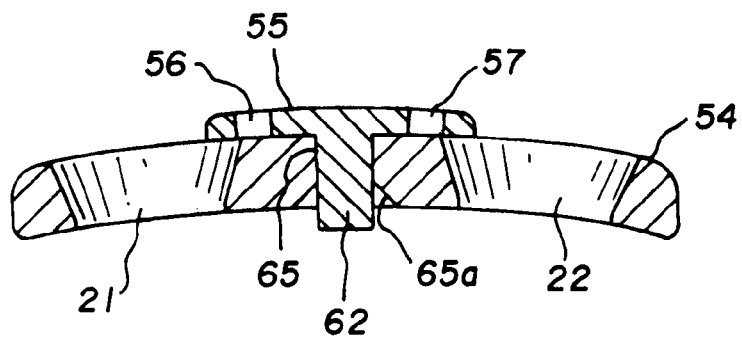
FIG. 18
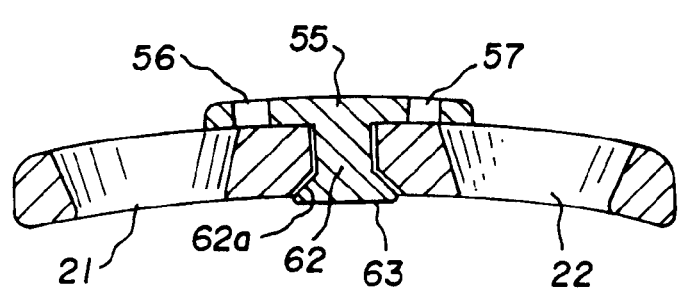

ANTERIOR CERVICAL PLATE

FIELD OF THE INVENTION

This invention relates to an anterior cervical plate, and in particular it relates to such a plate with a new and improved locking element.

BACKGROUND OF THE INVENTION

It is known to provide an anterior cervical plate for attachment to the anterior of two or more cervical vertebrae for the purpose of immobilizing, stabilizing and/or aligning those vertebrae. The plates can be used for a variety of conditions including for example providing added strength and rigidity after fusion of adjacent vertebrae, securing vertebrae together where an intervening vertebrae has been removed and replaced, correcting spinal deformities, and correcting instability caused by trauma, tumors, advanced degenerative discs, infection or congenital or acquired deformities.

Cervical plates of the present type are generally elongated so as to span the distance between two, three, four or more vertebrae, as required in a given situation. The plates are generally curved transversely so as to fit the curvature of the vertebrae to which they are attached. Additionally, plates of this type are generally concave longitudinally thereof to match the curvature of the cervical spine. Cervical plates of this type are provided with holes for bone screws. Holes are drilled into the adjacent vertebrae by instruments which are known in the art, after which the cervical plate is attached by bone screws which pass through the holes in the cervical plate for securing the plate to the adjacent vertebrae.

Many cervical plates of the present type are known, each having various arrangements for securing the bone screws. Such arrangements are shown in prior U.S. Pat. Nos. 5,364,399; 5,549,612; 6,193,721; 6,224,602; 6,235,034; 6,383,186; and 6,454,771. Notwithstanding the development of the prior art to date, a need exists for improvements in arrangements for securing the bone screws in place after the bone screws have secured the cervical plate onto the adjacent vertebrae.

SUMMARY OF THE INVENTION

It is a purpose of the present invention to provide an anterior cervical plate of the type for attachment to cervical vertebrae for stabilizing, immobilizing and/or aligning those vertebrae, which plate has a new and improved arrangement for securing the bone screws in place after the cervical plate has been attached to the cervical vertebrae.

In accordance with the present invention, the cervical plate includes a number of bone screw holes for attaching the cervical plate to the vertebrae. Specifically, in accordance with the present invention there is provided at least one pair of adjacent bone screw holes, preferably transversely aligned, wherein the cervical plate has a locking element mounted between the adjacent bone screw holes and movable between a first, open position where it uncovers the two bone screw holes to permit insertion therethrough of the bone screws and a second, locking position whereat the locking element overlies at least a portion of each of the two bone screw holes, to lock those bone screws in place. The locking element of the present invention is intended essentially to prevent the screws from backing out, i.e., it is not intended to be a force exerting member to exert a downward force on tightened bone screws.

In accordance with one arrangement of the present invention, an elongated locking element is pivotally mounted on a surface area of the cervical plate between two adjacent bone screw holes. This locking element is movable to a first position whereat it completely uncovers the two adjacent holes so as to permit the insertion of bone screws therethrough. The locking element is then arranged to be pivoted to partially cover the two bone screw holes with the bone screws secured in place therebeneath.

The present invention provides various arrangements for effecting the pivotal connection between the plate and the locking element. In one arrangement the plate may have a raised boss onto which is pivotally mounted a locking element having an opening therethrough. In another arrangement the plate itself can have an opening and the locking element can have a raised boss on the lower side thereof which projects through the through hole in the plate. In another arrangement, the locking element can have a central opening and the plate can have a through hole, both of which cooperate with a third element, a post which passes through the opening and the through hole.

Another feature of the present invention is the provision of a structure to positively position the locking element in its locking position. For this purpose, a protrusion on either the bottom of the locking element or the surface of the plate can be arranged to be snap fitted into a recess or indentation in the other of the cervical plate or locking element. Preferably, the protrusions will be in the form of bumps on the surface of the plate and the indentions will be in the form of recesses on the bottom of the locking element, wherein the bumps and recesses are aligned to positively position the locking element when it is in its locking position. The bottom of the locking element may include recessed ramps which ride over the bumps as the locking element is initially turned from its open position to its locking position. The bumps would then ride up the recessed ramps and then snap into place in the recesses when the locking element has reached its locking position.

Turning of the locking element between its open and locking positions can be accomplished by using a tool, and for this purpose the locking elements are provided with a pair of openings, offset relative to the pivot axis, to receive such a tool.

The present invention is applicable to cervical plates of a virtually limitless number of configurations. Cervical plates are generally referred to by the number of levels that they overlie, wherein the word "level" refers to the number of intervening intervertebral spaces that are spanned. Thus, for example, a three level cervical plate would span the four vertebrae beyond and between the three intervertebral spaces. The plate can be connected at some places by a single central bone screw through a single central bone screw hole instead of by the two adjacent bone screw holes which include the locking element of the present invention. In virtually all configurations, an opening will be provided between adjacent vertebrae for viewing the intervening intervertebral space.

In any configuration the cervical plate would almost always be attached to the upper and lower vertebrae. Connections of the cervical plate between the upper and lower vertebrae would depend on the level of the cervical plate and the nature of the surgery performed on the spine adjacent to the cervical plate. For example, if the surgery involved replacing only the discs and leaving the vertebrae intact in a three or four level cervical plate, then screws might be attached to the intermediate vertebrae. However, a long plate such as a three level or four level plate would more likely be used after a corpectomy, wherein the intervening vertebrae and discs would have been removed and replaced with a bone plug/graft or a mesh/cage implant. In these cases, it is unlikely that screws would be attached between the upper and lower vertebrae, although it might be desirable to place one or two screws into a bone plug/graft.

Thus, it is an object of the present invention to provide a new and improved anterior cervical plate.

It is another object of the present invention to provide a new and improved locking element in combination with a cervical plate for locking a pair of bone screws in adjacent bone screw openings of the plate.

These and other objects of the present invention will be apparent from the detailed description to follow, together with the accompanying drawings.

BRIEF DESCRIPTION OF THE DRAWINGS

There follows a detailed description of preferred embodiments of the present invention which are to be read together with the drawings wherein:

FIG. 16 is a bottom perspective view of the locking element of FIG. 12;

FIG. 17 is a view taken along line 18-18 of FIG. 12, but showing certain elements in a partially assembled state;

FIG. 18 is a cross sectional view taken along line 18-18 of FIG. 12;

DETAILED DESCRIPTION OF THE PREFERRED EMBODIMENTS

Referring now to the figures, like elements are represented by like numerals throughout the several views.

Figure 22:
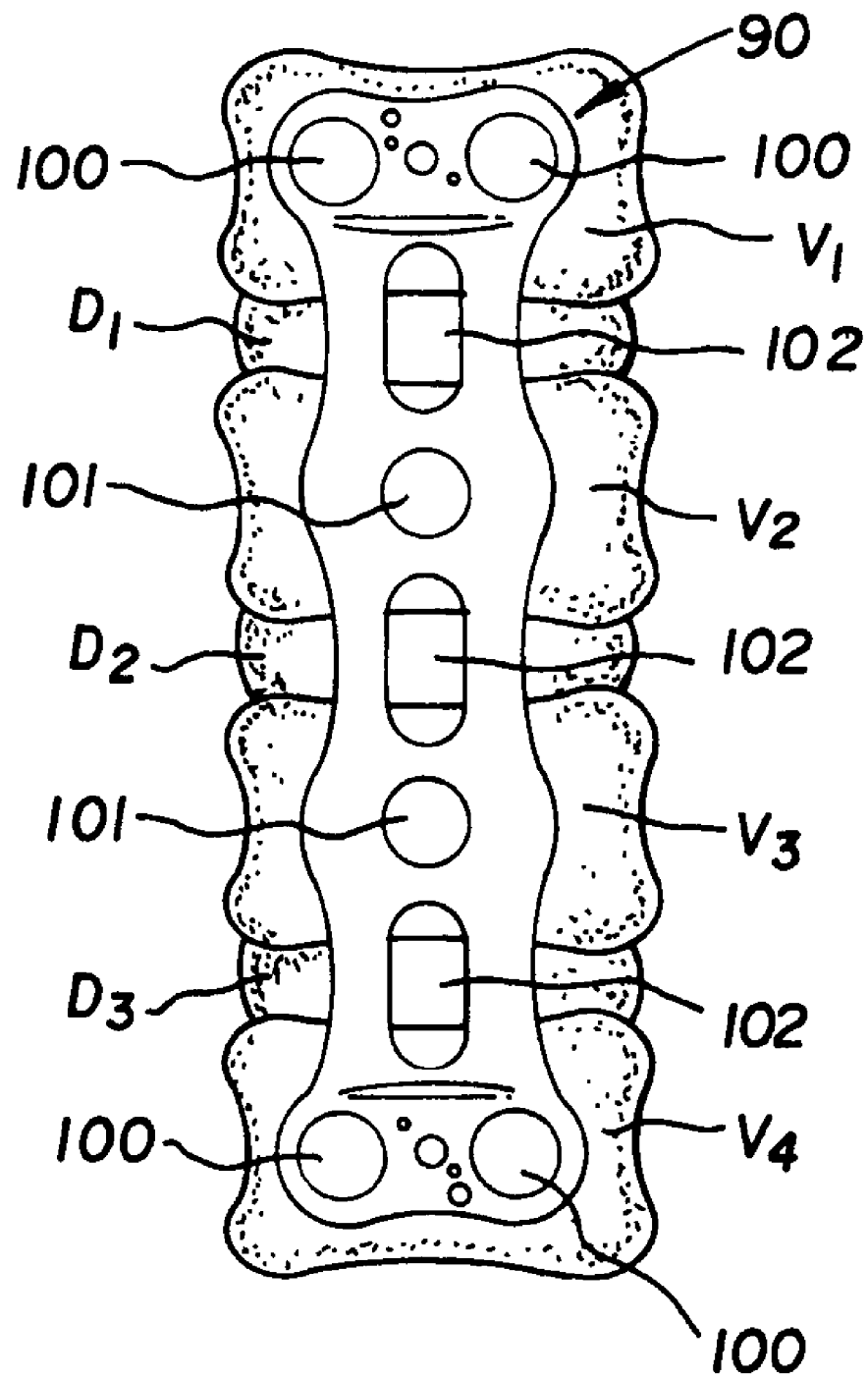
FIG. 22 is a schematic view showing an anterior cervical plate which would in the final form include the features of the present invention, but showing the plate in relation to vertebrae and discs of the cervical spine.

An anterior cervical plate of the type with which the present invention is concerned attaches to the anterior surface of a plurality of cervical vertebrae to perform a number of different functions including stabilizing, aligning and immobilizing two or more adjacent vertebrae. These will be described generally with respect to the diagrammatic view of FIG. 22. This figure shows four adjacent vertebrae V1, V2, V3 and V4 separated by intervertebral discs D1, D2 and D3, respectively. Cervical plates are defined by "levels" wherein the term "level" designates the number of intervertebral disc spaces which are traversed by the cervical plate. Thus for example the cervical plate 90 shown in FIG. 22 spans three different intervertebral spaces D1, D2 and D3 between vertebral bodies V1, V2, V3 and V4 so that the embodiment shown therein is a three level plate. Cervical plates can come in a longer size, i.e., up to four levels or of course in smaller sizes, i.e., two levels or one level. For convenience, the invention is described throughout the present specification with respect to one level and two level cervical plates. It is to be understood that strictly for purposes of illustration FIG. 22 shows the cervical plate 90 against what appears to be an essentially normal spine. In practice, however, as discussed above, when the cervical plate is attached, it will be subsequent to surgery that may have replaced some or all of the intermediary discs and vertebrae with a corpectomy to remove vertebrae which is replaced with a bone graph/plug or a mesh/cage implant or the like.

A cervical plate can have different openings serving different purposes. In FIG. 22 the pair of holes 100 are provided for attaching two bone screws to the upper and lower vertebrae adjacent thereto is the form of bone screw holes to which the locking element of the present invention will be applied. However, in combination with bone screw holes 100, the cervical plate can have other bone screw holes such as simple holes 101 which are shown in FIG. 22 for attachment if desired, between the upper and lower bone screw holes 100. Between the attachments to the vertebral bodies the cervical plates are provided with openings 102 which serve as windows to view into the interior of the intervertebral spaces. There will generally be at least one such window opening in the vicinity of each intervertebral space. As is known, anterior cervical plates of this type, in the various configurations, can be used to stabilize, immobilize and/or align the cervical spine following a number of different problems. For example, intermediate disc or discs can be removed and replaced by a cage, mesh or bone graph/plug or allograft/autograft. In addition to removal of the discs, the intermediate vertebrae can also be removed. The cervical plate can also be used to correct instability of the cervical spine caused by trauma, tumors, advanced degenerative discs disease, cervical deformities caused by lordosis or kyphosis or other conditions.

FIGS. 1-7 illustrate a first embodiment of the present invention. These figures illustrate an anterior cervical plate 10 which has first, second and third recessed areas 11, 12 and 13 for receiving bone screws through holes 17, 18; 19, 20; and 21, 22, respectively. Between the recessed areas 11, 12 and 13 are provided web areas 15 and 16, respectively, each including a window opening 28 and 29, respectively, for viewing the intervertebral space adjacent thereto, as described above. In practice, each of the pair of bone screw holes would have a locking element 30 mounted therebetween. For purposes of illustration, in the first embodiment, i.e., FIGS. 1, 2 and 5-7, the top recessed area 11 includes a locking element 30 in the open position, the bottom recessed area 13 shows a locking element 30 in the locking position and the middle recessed area 12 does not show any locking element, so as to illustrate the recessed area there below.

Figure 1:
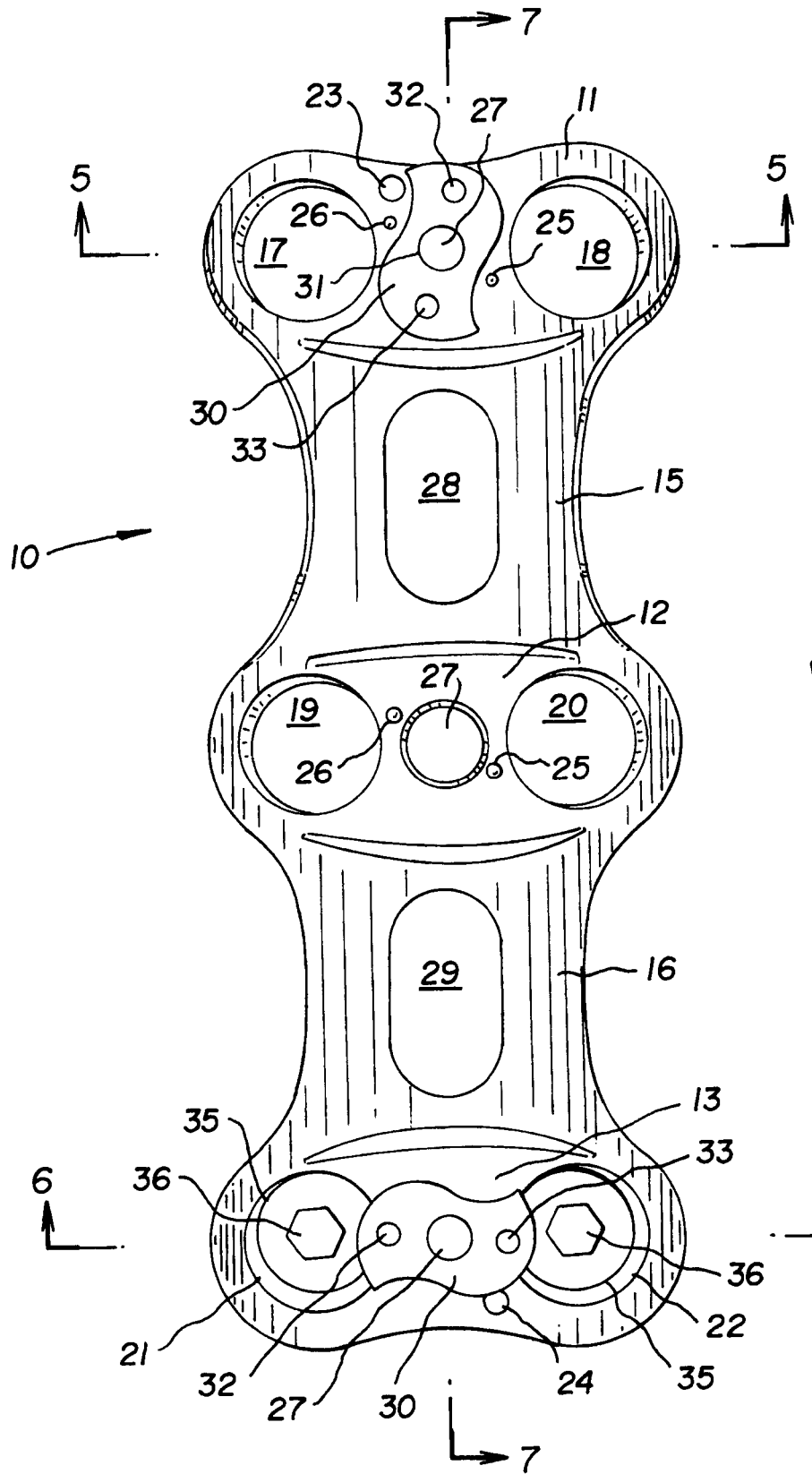
FIG. 1 is a top plan view of an anterior cervical plate in accordance with the present invention.
Figure 2:
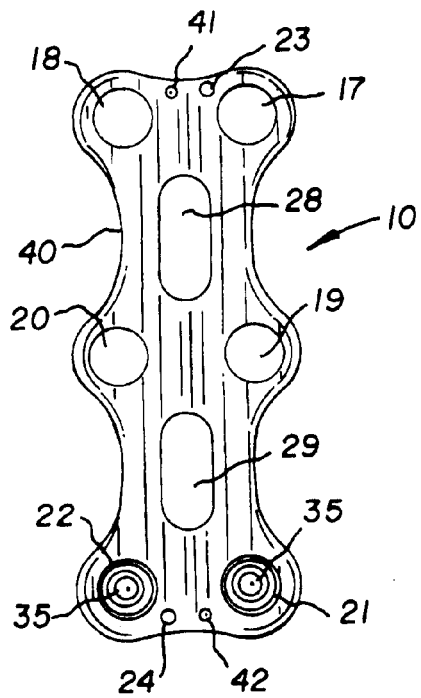
FIG. 2 is a bottom plan view of FIG. 1.

Referring to FIG. 1 and the bottom plan view of FIG. 2, the plates include spikes 41, 42 for initially engaging the vertebrae when the cervical plate is first mounted thereon. Some operators prefer to use a fixation pin in addition to the spikes 41, 42, and for this purpose the cervical plate 10 is provided with openings 23 and 24 at the top and bottom thereof, respectively.

Figure 6:
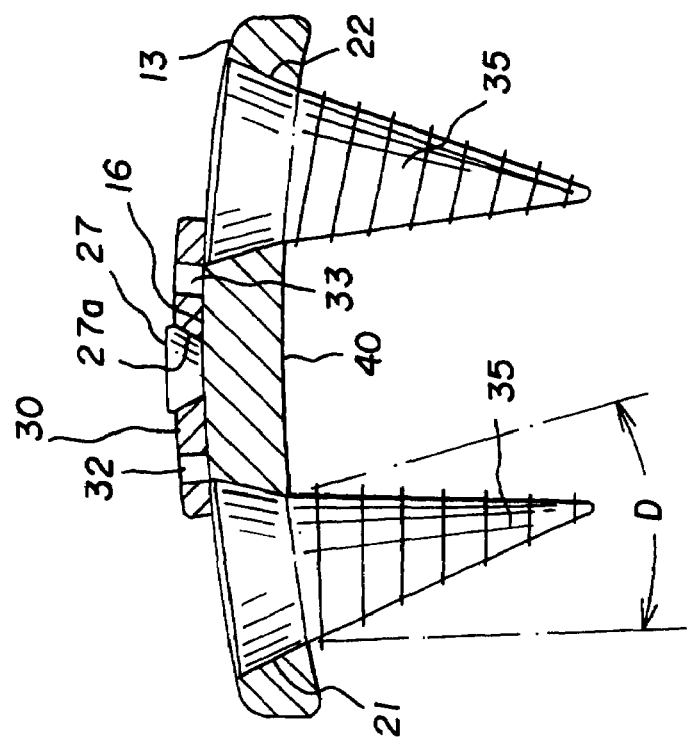
FIG. 6 is a cross sectional view taken along line 6-6 of FIG. 1.
Figure 5:
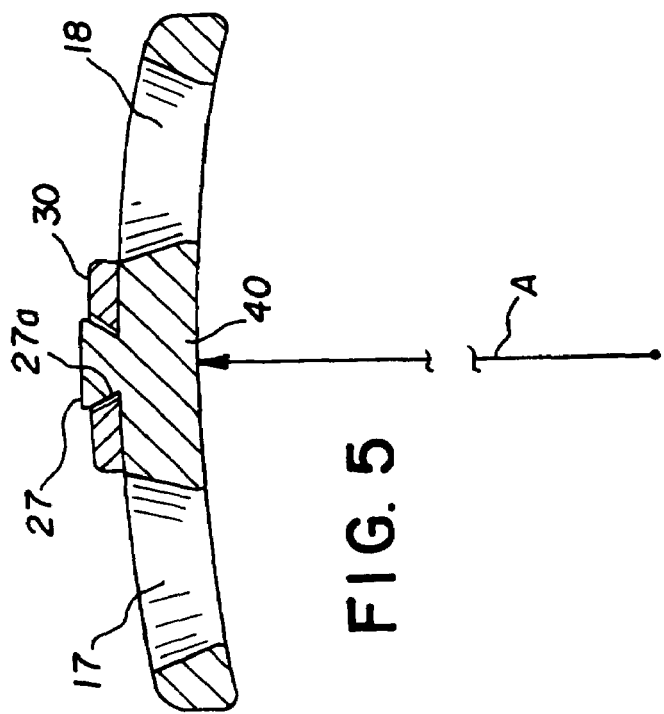
FIG. 5 is a cross sectional view taken along line 5-5 of FIG. 1.
Figure 7:
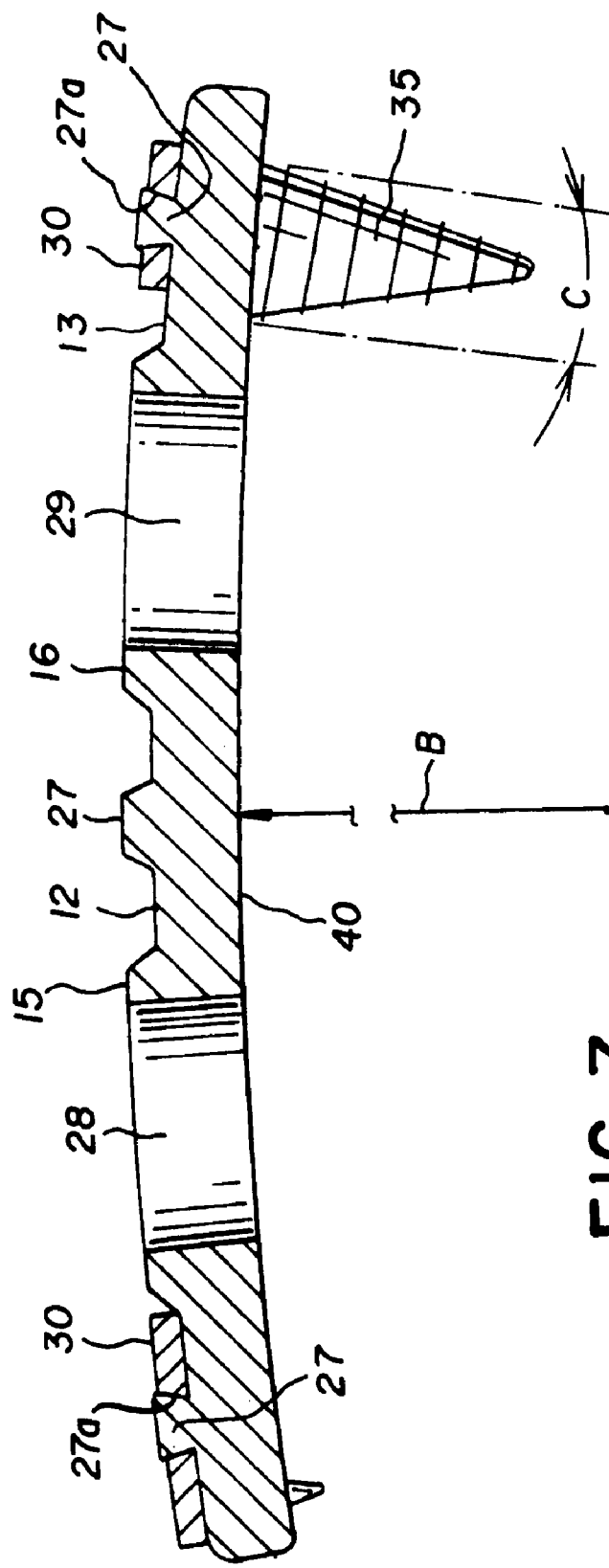
FIG. 7 is a cross sectional view taken along line 7-7 of FIG. 1.

Referring to FIGS. 1, 6 and 7, the lower bone screw holes 21 and 22 each have a bone screw 35 therein, each having a bone screw socket 36 for receiving a screwdriver for securing the bone screws into the bone. Referring to FIGS. 6 and 7, in a manner known per se, the screws can be driven into the bone over a range of transverse angles D, as shown in FIG. 6, or longitudinal angles C, as shown in FIG. 7. Normally the range of the angles C and D is approximately 15°. Referring to FIGS. 5 and 7, the cervical plates would generally be curved in both the transverse and the longitudinal direction. The radius of curvature of the plate in the transverse direction would be approximately 24 mm, as represented by arrow A, in order to fit the curvature of the vertebral bodies. Referring to FIG. 7, the radius of curvature of the cervical plate in the longitudinal direction would be approximately 200 mm, as represented by arrow B.

Figure 3:
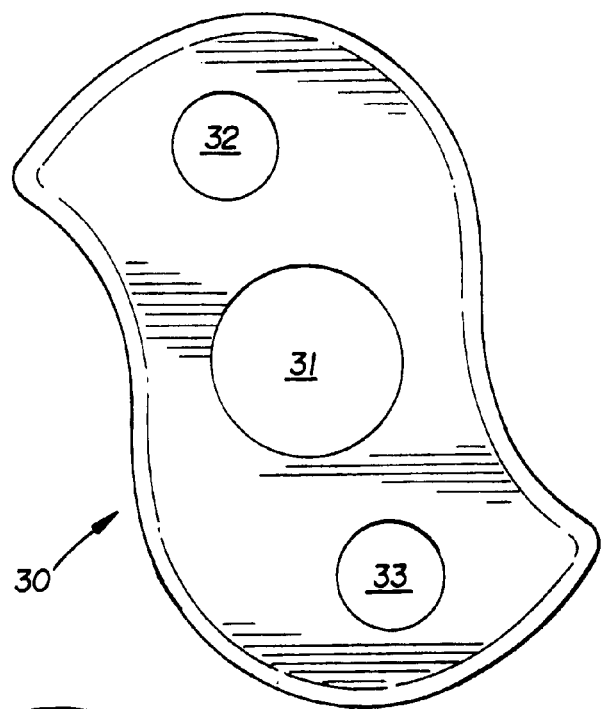
FIG. 3 is a top plan view of the locking element of FIG. 1.
Figure 4:
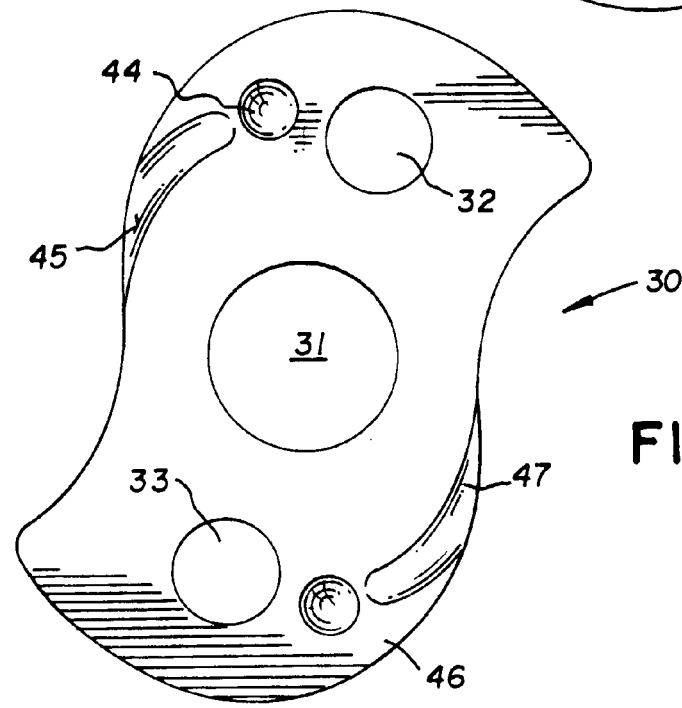
FIG. 4 is a bottom plan view of the locking element of FIG. 1.

A feature of the present invention is an elongated locking element 30 which is mounted so as to move between an open position as shown at recessed area 11 of FIG. 1 and a locking position as shown at the lower recessed area 13 of FIG. 1. Referring to FIGS. 3 and 4, the locking element 30 includes a central hole 31 for engaging the boss 27 on the cervical plate 10 and additional openings 32 and 33 offset from the pivot axis for receiving a tool to assist in turning the locking element 30 between its open and locking positions. To positively position the locking element 30 in its locked position, a pair of bumps 25 and 26 on the cervical plate are positioned to engage recesses 44 and 46, as shown in FIG. 4, on the bottom of the locking element 30. To facilitate movement of the locking element over the bumps 25 and 26, the bottom of the locking element 30 includes recessed inclined ramps 45 and 47 which are deep enough to initially ride over the tops of the bumps. The ramps stop short of the recesses 44 and 46 so that as the locking element 30 is turned, the bumps 25, 26 will ride up the ramps and then snap into place in the recesses 44 and 46.

The embodiment of FIGS. 1-7 illustrates a first arrangement for attaching the locking element to the boss 27. It is noted that the center boss 27 in recessed area 12 is essentially frustoconical. When it is desired to attach a locking element 30 to a boss 27, the locking element is placed thereon after which the top of the boss 27 is swaged, as shown at 27a in FIGS. 5, 6 and 7, so as to prevent removal of the locking element while allowing it to pivot thereabout.

Figure 8:
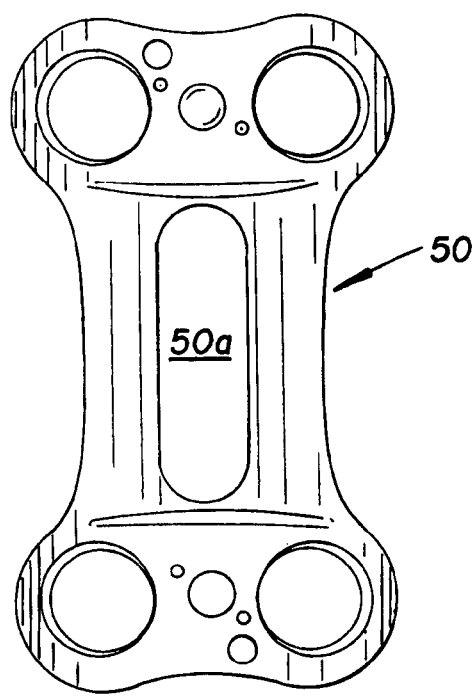
FIGS. 8, 9, 10 and 11 show four different shaped anterior cervical plates, all of which are designed to employ the features of the present invention.
Figure 9:
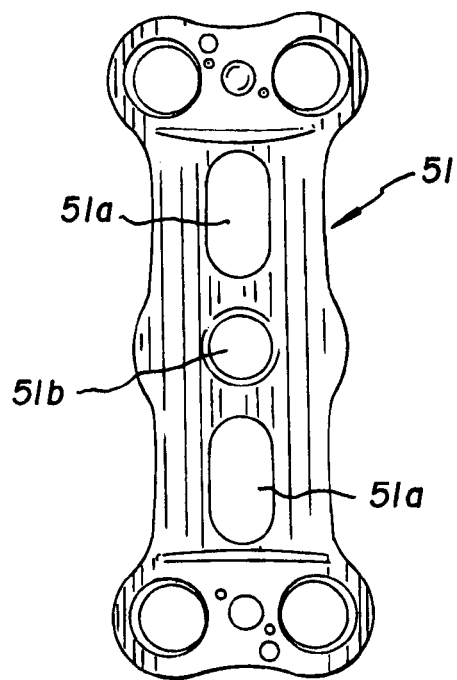
Figure 10:
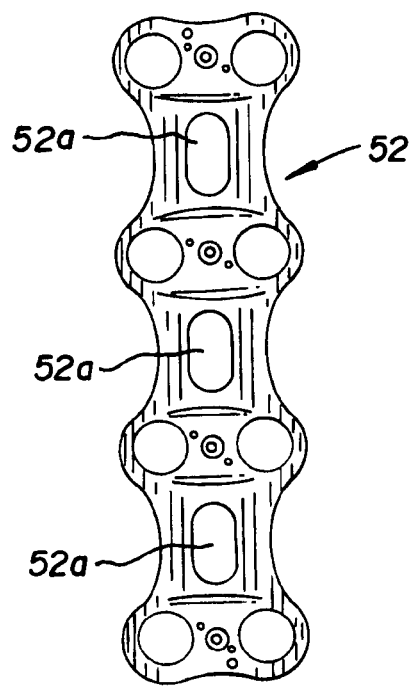
Figure 11:
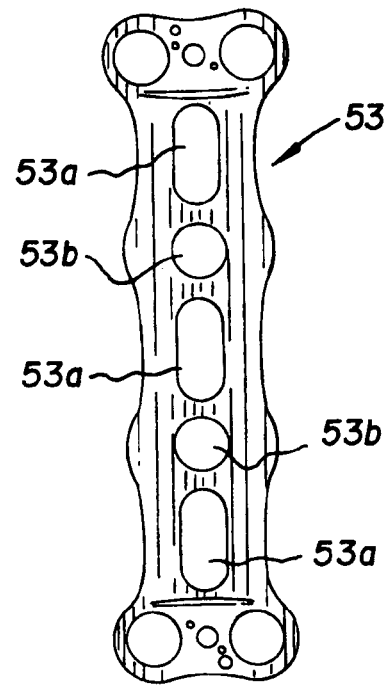

FIGS. 8, 9, 10 and 11 are intended to show various shapes of anterior cervical plates, each intended for a different level and/or showing a different connection and some such as FIG. 9 and FIG. 11 showing simple bone screw holes for attachment to certain intervening vertebrae.

Cervical plate 50 of FIG. 8 is a two level cervical plate having pairs of bone screw holes at the two ends thereof which would in practice incorporate the features of the present invention and including a window opening 50a for viewing the intervertebral space therebetween. FIG. 9 illustrates another cervical plate 51 which also would include the features of the present invention at the pairs of holes at the top and bottom thereof. This is a two level cervical plate having viewing holes 51a for viewing the intervertebral spaces and a simple central bone screw hole 51b. FIG. 10 illustrates a three level cervical plate 52 having the pair of bone screw holes which could receive the locking element of the present invention at all four connections to the vertebrae, and showing window opening 52a for viewing the three intermediate intervertebral spaces. FIG. 11 shows a cervical plate 53 which is the same one previously described with respect to FIG. 22, and having three viewing windows 53a and two simple bone screw holes 53b.

FIGS. 12-18 illustrate another embodiment of the present invention which is identical in all respects to the embodiment of FIGS. 1-12 with respect to the features of the locking element (and other than the fact that some of the embodiments of FIGS. 1-12 show different shapes and arrangements of cervical plates), except for a different arrangement for connecting the locking element to the cervical plate.

Figures 12, 13:
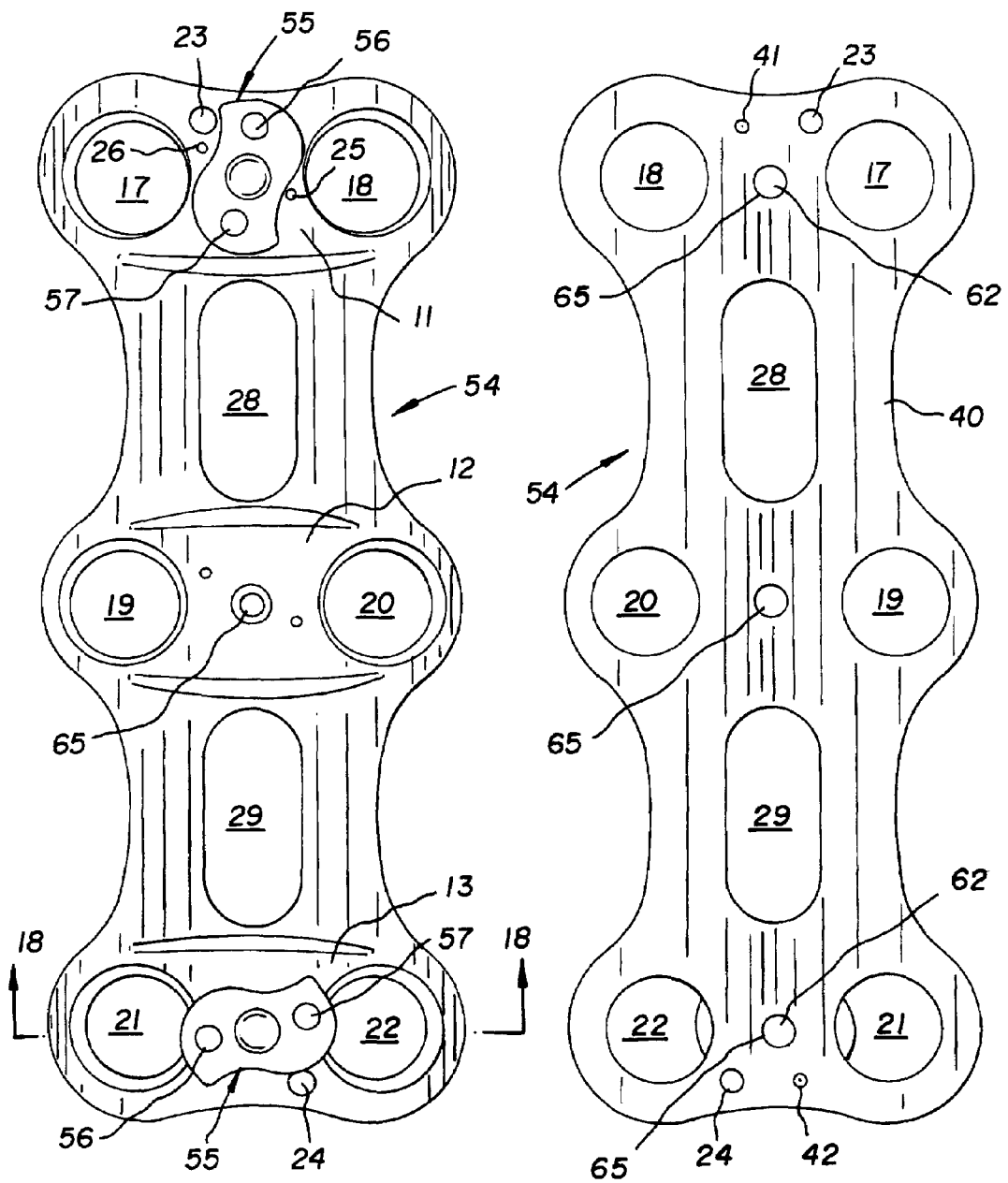
FIG. 12 is a top plan view of an anterior cervical plate showing another embodiment of the present invention.
FIG. 13 is a bottom plan view of FIG. 12.
Figure 14:
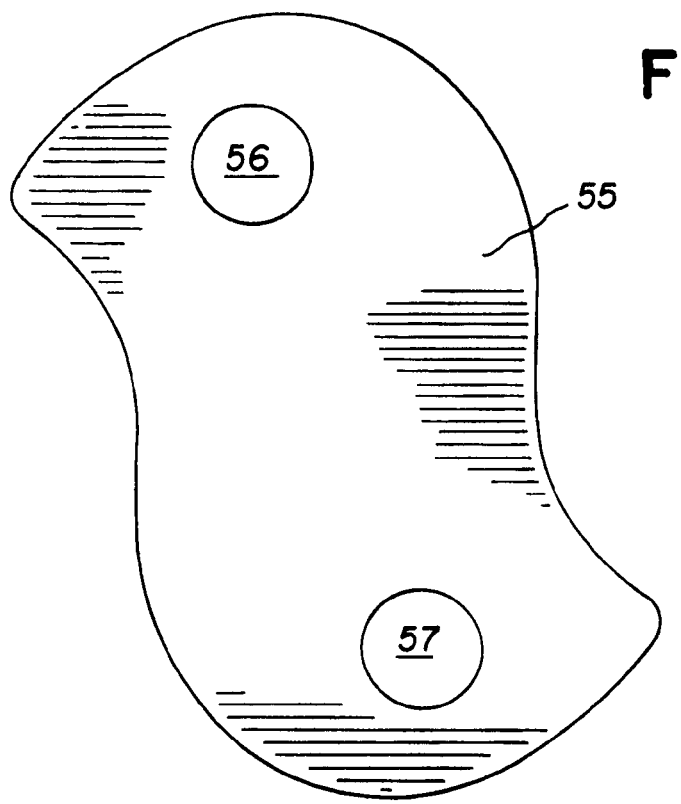
FIG. 14 is a top plan view of the locking element of FIG. 12.
Figure 15:
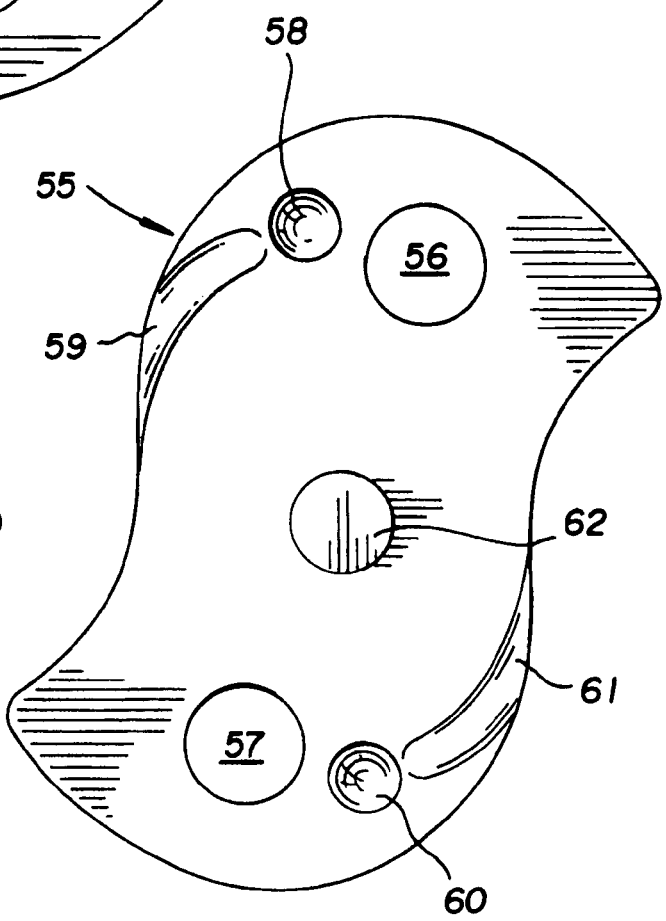
FIG. 15 is a bottom plan view of the locking element of FIG. 12.

For convenience, FIGS. 12-18 use the same numerals as in FIGS. 1-7 for identical parts. Different numerals are used with respect to the modified locking element. As seen in FIGS. 12 and 13, in this case the recessed areas 11, 12 and 13 which receive the locking element include a through hole 65 instead of raised boss 27. The locking element 55, as shown in FIGS. 14-16, instead of having the opening 31 in the center thereof, has a raised boss 62 on the bottom thereof. This locking element 55 includes tool receiving holes 56 and 57 which are similar to holes 32 and 33 of FIGS. 1-7. In a manner similar to the embodiment of FIGS. 1-7, in this locking element 55 there are provided recesses 58 and 60 for cooperating with bumps 25 and 26 and recessed ramps 59 and 61 for riding up over the bumps and allowing the bumps to snap into place into the recesses 58 and 60, precisely as described above with respect to FIGS. 1-7.

Referring to FIG. 17, the through hole 65 has a chamfer 65a at the bottom thereof. FIG. 17 illustrates the locking element 55 with a boss 62 still of the shape as shown in FIGS. 15 and 16, extending through the opening 65. The assembly process, however, is completed by swaging the lower end of the boss 62 as shown at 62a in FIG. 18 to secure the locking element 55 onto the plate 54 while allowing it to pivot relative to the plate 54.

Figure 19:
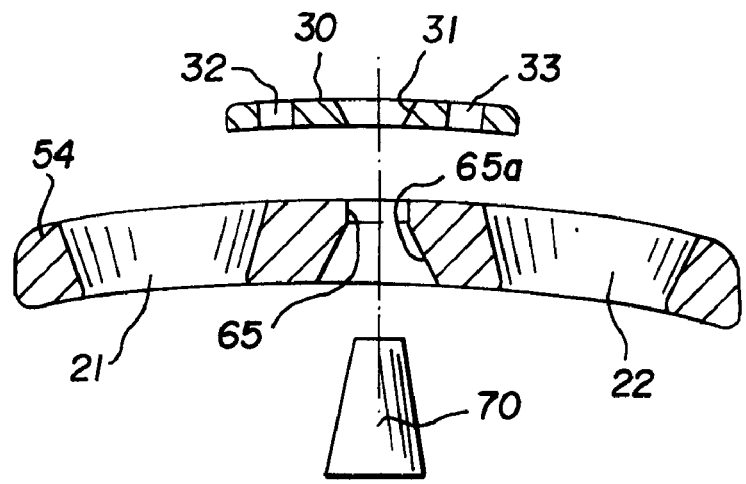
FIG. 19 is an exploded view which is taken along a plane represented by plane 18-18 of FIG. 12 but showing a modification of the present invention.
Figure 20:
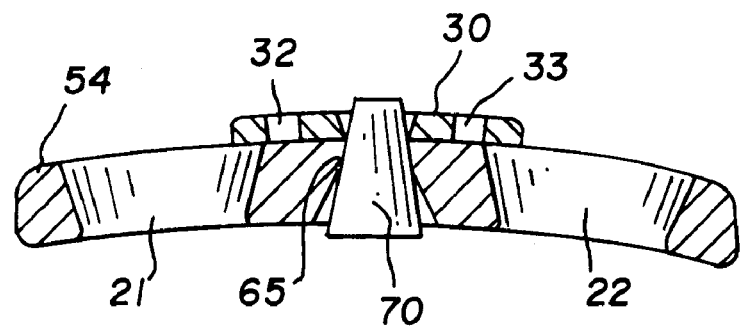
FIG. 20 illustrates the embodiment of FIG. 19, but during a subsequent state of assembly.
Figure 21:
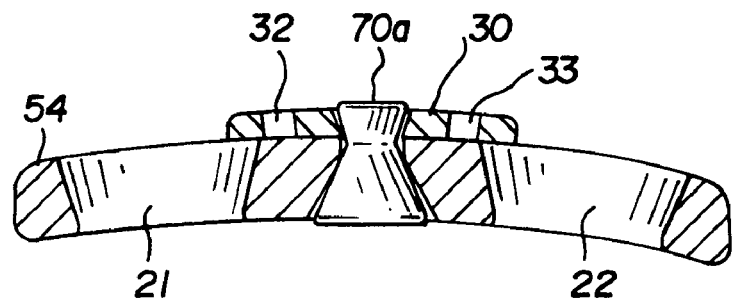
FIG. 21 shows the modification of FIGS. 19 and 20 in the fully assembled state.

FIGS. 19-21 illustrate the anterior cervical plate 54 taken along plane 18-18 of FIG. 12 but showing a modified attachment between the locking element and the cervical plate. Referring to FIG. 19, the locking element is of the type 30 shown in FIGS. 1-7 with an opening 31 therein. The plate is of the type 54 shown in FIGS. 12-17 with a through hole 65 having a chamfer 65a. In this embodiment, a tapered post 70 is inserted up through the through hole 65 such that its conical surface engages the chamfer 65a with the upper end of post 70 located above the upper surface of locking element 30 as shown in FIG. 20. The post 70 is then fixed to the plate at its bottom and swaged at the top as shown at 70a in FIG. 21 in order to allow the locking element 30 to pivot relative to the cervical plate 54.

Although the operation of the present invention will be apparent from the preceding discussion, for convenience the operation will be summarized herein. First, after the problem of the cervical spine has been surgically repaired, the anterior cervical plate is placed against the anterior of the cervical vertebrae. Initially it is held there by the spikes 41, 42 and/or by fixation pins passing through the openings 23, 24. The method of preparing the holes in the vertebral bodies for the bone screws is well known, conventional and need not be further described herein.

At the recessed areas which include the locking element of the present invention, the screws are tightened to the point where their upper surfaces are at or slightly below the level of the recessed areas so that the locking elements, when pivoted to the locking position, will prevent the screws from backing out but not exert an inward force thereon. The bone screws for the holes adjacent the locking elements are inserted and attached when the locking element 30 or 55 is in the open position as shown at the top of FIGS. 1 and 12. After the bone screws are tightened in place, a tool (not shown) engages the openings 32 and 33 or 56 and 57 to turn the locking element clockwise. On the bottom of the locking element, ramps 44, 47 or 59, 61 on the bottom of the locking element will ride up the bumps 25, 26 until the locking element moves to its locking position as shown at the bottom recessed area 13 of FIGS. 1 and 12. At this point the bumps 25 and 26 have snapped into their respective recesses 44 and 46 for locking element 30 and 58 and 60 for locking element 55. A preferred material for the cervical plate would be implantable Titanium alloy, Ti-6 Al-4V per ASTM F-136.

Although the invention has been described in considerable detail with respect to preferred embodiments, it will be apparent that the invention is capable of numerous modifications and variations, apparent to those skilled in the art, without departing from the spirit and scope of the invention.

What is claimed is:

1. An anterior cervical plate for engaging at least two vertebrae along the anterior cervical spine, comprising:
   a lower surface adapted to engage the anterior of at least two cervical vertebrae and an opposite upper surface,
   at least one receiving area formed in the upper surface and including two transversely aligned screw holes, and
   a locking element pivotally mounted on the receiving area, the locking element being elongated and including tool engaging means offset from the pivot axis for grasping and pivoting the locking element, the locking element being movable to a first position in which the locking element completely uncovers the screw holes and a second position in which the ends of the elongated locking element extend over a portion of both screw holes to prevent the bone screws located therein from backing out;
   wherein the plate has a raised boss and the locking element has an opening which is pivotally mounted on the raised boss.

2. A cervical plate according to claim 1, wherein the plate has a through hole therethrough and the locking element has a raised boss on the bottom thereof extending into the through hole of the plate and connected therein such that the locking element is pivotally mounted on the plate.

3. An anterior cervical plate for engaging at least two vertebrae along the anterior cervical spine, comprising:
   a lower surface adapted to engage the anterior of at least two cervical vertebrae and an opposite upper surface,
   at least one receiving area formed in the upper surface and including two transversely aligned screw holes, and
   a locking element pivotally mounted on the receiving area, the locking element being elongated and including tool engaging means offset from the pivot axis for grasping and pivoting the locking element, the locking element being movable to a first position in which the locking element completely uncovers the screw holes and a second position in which the ends of the elongated locking element extend over a portion of both screw holes to prevent the bone screws located therein from backing out;
   wherein one of the receiving area and bottom of the locking element has at least one projection, the other of the receiving area and bottom of the locking element having at least one recess which is positioned to receive the projection and thereby snap the locking element onto the receiving area when the locking element is in said second position.

4. A cervical plate according to claim 3, wherein the receiving area or the locking element which has the recess also has a ramp to ride up over the projection and permit the projection to snap into the recess when the locking element reaches its second position.

5. A cervical plate according to claim 4, wherein the at least one projection is on the receiving area and the at least one recess is on the bottom of the locking element.

6. A cervical plate according to claim 4, including a recessed ramp on the bottom of the locking element for riding up over the projections on the receiving area and permitting the projections to snap into place in the recesses when the locking element is in the second position.

7. A cervical plate according to claim 3 wherein the tool engaging means comprises a pair of tool receiving openings in the locking element for receiving a tool to turn the locking element between the first and second positions.

8. An anterior cervical plate for engaging at least two vertebrae along the anterior cervical spine, comprising:
   a lower surface adapted to engage the anterior of at least two cervical vertebrae and an opposite upper surface,
   at least one receiving area formed in the upper surface and including two transversely aligned screw holes, and
   a locking element pivotally mounted on the receiving area, the locking element being elongated and including tool engaging means offset from the pivot axis for grasping and pivoting the locking element, the locking element being movable to a first position in which the locking element completely uncovers the screw holes and a second position in which the ends of the elongated locking element extend over a portion of both screw holes to prevent the bone screws located therein from backing out;
   wherein the receiving area is a recessed area relative to other raised web areas of the plate, and including a pair of projections on the recessed receiving area and a pair of matching recesses on the bottom of the locking element, wherein the projections will snap into place in the recesses when the locking element is in said second position.

9. A cervical plate according to claim 8, wherein the locking element has a pair of recessed ramps on the bottom thereof to ride up over the projections and permit the projections to snap into place in the recesses.

10. An anterior cervical plate, for engaging at least two vertebrae along the anterior cervical spine, comprising:
    a plate having a lower surface adapted to engage the anterior of at least two cervical vertebrae and an opposite upper surface,
    at least one pair of spaced apart screw holes through the plate,
    a locking element pivotally mounted between the screw holes and movable between a first position in which the locking element completely uncovers the screw holes and a second position in which the locking element extends over a portion of both screw holes to prevent the bone screws located therein from backing out, and
    a positive positioning structure which holds the locking element in the second position wherein the positive positioning structure comprises a projection on one of the plate or locking element and a matching recess on the other of the plate or locking element, the projection and the matching recess being positioned so as to hold the locking element in said second position.

11. A cervical plate according to claim 10, wherein the projection is on the plate and the matching recess is on the bottom of the locking element.

12. A cervical plate according to claim 11, wherein the bottom of the locking element has a recessed ramp to ride up over the projection to permit the projection to snap into the matching recess when the locking element is in the second position.

13. A cervical plate according to claim 12, including a pair of projections on the plate and a pair of matching recesses on the bottom of the locking element.

14. A cervical plate according to claim 10, wherein the plate has a raised boss and the locking element has an opening which is pivotally mounted on the raised boss.

15. A cervical plate according to claim 10, wherein the plate has a through hole and the locking element has a raised boss on the bottom thereof extending into the through hole of the plate and connected therein such that the locking element is pivotally mounted on the plate.

16. A cervical plate according to claim 10, wherein the plate has a through hole which is aligned with an opening through the locking element, and a separate post is located in both the through hole and the opening and attached to the plate and allowing the locking element to pivot relative thereto.

* * * * *